United States Patent
Berney, IV et al.

(10) Patent No.: US 10,125,464 B2
(45) Date of Patent: Nov. 13, 2018

(54) PHOTOGRAMMETRIC SOIL DENSITY SYSTEM AND METHOD

(71) Applicant: The United States of America as Represented by The Secretary of The Army, Washington, DC (US)

(72) Inventors: Ernest S. Berney, IV, Vicksburg, MS (US); Thad C. Pratt, Vicksburg, MS (US); Naveen B. Ganesh, Vicksburg, MS (US)

(73) Assignee: The United States of America as Represented by The Secretary of The Army, Washington, DC (US)

( * ) Notice: Subject to any disclaimer, the term of this patent is extended or adjusted under 35 U.S.C. 154(b) by 0 days.

(21) Appl. No.: 15/069,810

(22) Filed: Mar. 14, 2016

(65) Prior Publication Data

US 2017/0260711 A1    Sep. 14, 2017

(51) Int. Cl.
| | |
|---|---|
| *G06K 9/00* | (2006.01) |
| *E02D 1/02* | (2006.01) |
| *G06T 7/00* | (2017.01) |
| *G06T 7/60* | (2017.01) |
| *G06K 9/46* | (2006.01) |
| *E02D 1/04* | (2006.01) |
| *G01N 33/24* | (2006.01) |

(52) U.S. Cl.
CPC ............ *E02D 1/025* (2013.01); *E02D 1/027* (2013.01); *E02D 1/04* (2013.01); *G01N 33/24* (2013.01); *G06K 9/0063* (2013.01); *G06K 9/4604* (2013.01); *G06T 7/0004* (2013.01); *G06T 7/602* (2013.01); *G06T 2207/30181* (2013.01)

(58) Field of Classification Search
None
See application file for complete search history.

(56) References Cited

U.S. PATENT DOCUMENTS

| | | | | |
|---|---|---|---|---|
| 2012/0304763 A1* | 12/2012 | Troxler | ............. | G01B 11/00 73/32 R |
| 2015/0096368 A1* | 4/2015 | O'Brien | ............. | E02D 1/00 73/32 A |
| 2015/0316526 A1* | 11/2015 | Kimmel | ............. | G01N 33/24 73/818 |

OTHER PUBLICATIONS

A photogrammetric method for calculating soil bulk density, by Bauer et al., Journal of plant nutrition and soil science—May 2014.*

* cited by examiner

*Primary Examiner* — Vikkram Bali
(74) *Attorney, Agent, or Firm* — Brian C. Jones

(57) ABSTRACT

The present invention is an apparatus which executes a photogrammetry method for calculating soil density. After a user excavates soil, measures the mass of the excavated soil and takes multiple images of the excavation site in combination with a calibration object, a data processor uses the various values obtained from the collected images to create a point cloud data object. The processor used this point cloud data object to create a visual representation of the hole. The processor rotates and scales the visual representation. The processor also uses the point cloud data object in volumetric calculations to determine the volume of the hole. Together with the soil mass, the volume allows calculation of soil density.

12 Claims, 6 Drawing Sheets

US 10,125,464 B2

PHOTOGRAMMETRIC SOIL DENSITY SYSTEM AND METHOD

STATEMENT REGARDING FEDERALLY SPONSORED RESEARCH OR DEVELOPMENT

The invention described herein was made by an employee of the United States Government and may be manufactured and used by the Government of the United States of America for governmental purposes without the payment of any royalties thereon or therefore.

BACKGROUND OF THE INVENTION

1. Field of Invention

This invention relates to the field of image analysis and more specifically to image enhancement and restoration.

2. Description of Related Art

Soil density is a critical factor when designing or building structures, or excavating for construction. If a structure stands on soil with a low or extremely variable density, it can collapse, sink, deform or otherwise become unsafe. Architects and engineers must either redesign a structure to fit a particular soil density or alter the soil density to ensure stable structural footing. Either scenario requires first testing the soil to determine density.

Nuclear density gauges (NDG) are the fastest density testing systems, requiring less than 5 minutes to conduct an individual test. An NDG uses nuclear sources to determine bulk soil density and water mass within the soil. These radioactive sources present a health risk to users and a danger if stolen for illegal purposes, requiring constant monitoring of users' radiation exposure levels and storage under high security. Transport of an NDG requires significant paperwork and can be difficult in both the US and around the world.

Volume replacement systems require the user to excavate a hole and fill it with calibrated materials. The technique is laborious and time intensive, and limited in the hole size useable. Users must transport calibrated materials to the site. To obtain an accurate volume, the calibrated materials must fill all the gaps in the hole, which may prove difficult for coarser soils. Adding the calibrated materials to the hole may enlarge the hole, making any resulting data inaccurate.

Electronic devices require pre-calibration to the soil of interest before returning a useable soil density to the operator. Device calibration requires use of a secondary density device such as a volume replacement system or NDG, or laboratory work requiring several days of testing the soil of interest. Calibration increases expense, labor and time, limiting the usefulness of these devices to continuous testing on a single soil.

There is an unmet need in the art for an accurate, easily used soil density measurement system that does not require extensive calibration, or significant health, safety, or security measures.

BRIEF SUMMARY OF THE INVENTION

The present invention is an apparatus for analyzing soil density utilizing a user-selected ground plane. The apparatus is a data processor configured with software to perform a photogrammetry method. First, the photogrammetry method receives a soil mass value M of excavated soil. Next, the photogrammetry method receives a variant image set of a calibration object and excavation site. The photogrammetry method then creates a point cloud from the variant image set. Next, the photogrammetry method instantiates a point cloud data object with point cloud data values to display a visual representation of the excavation site and the calibration object on a graphic user interface (GUI). The photogrammetry method then updates the point cloud data values using an autorotation method to orient the visual representation on the GUI. Next, the photogrammetry method updates the point cloud data values using a scaling method to scale the visual representation on the GUI. The photogrammetry method then displays a visual representation of the point cloud data object on the GUI. Next, the photogrammetry method receives plane coordinate values for a user-selected ground plane. The photogrammetry method then calculates an excavated volume $V_h$ using a cubic volumetric method, wherein the plane coordinate values are utilized to define at least one boundary of a volumetric cube utilized in the cubic volumetric method. Next, the photogrammetry method calculates a soil density value D using the excavated volume $V_h$ and the soil mass value M. The photogrammetry method then displays the soil density value D on the GUI.

BRIEF DESCRIPTION OF SEVERAL VIEWS OF THE DRAWING(S)

TERMS OF ART

As used herein, the term "autorotation method" means a method for adjusting the relative angulation of a visual representation.

As used herein, the term "calibration object" means an object of known dimensions.

As used herein, the term "cubic volumetric method" means a method for determining the volume of an excavation site using at least one volumetric cube.

As used herein, the term "excavated volume" means a volume of soil removed from an excavation site.

As used herein, the term "excavation site" means a location from which soil is removed.

As used herein, the term "plane coordinate values" means the values of coordinates of a ground plane.

As used herein, the term "point cloud" means a data set containing three dimensional information extracted from two or more images of the same object. This information may include, but is not limited to, a quasi-unique set of coordinate values along the X-, Y- and Z-axis and/or a quasi-unique set of color levels using red, green and blue levels, denoted as R, G and B, respectively.

As used herein, the term "scaling method" means a method for adjusting the relative location of points in a visual representation.

As used herein, the term "soil density" means the bulk density of soil.

As used herein, the term "soil mass value" means the mass of an excavated volume of soil.

As used herein, the term "variant image set" means more than one image of the same subject matter wherein each image is adjusted for a particular variable including but not limited to magnification, elevation and angle.

As used herein, the term "user-selected ground plane" means a horizontal plane selected by a user and extending parallel to a ground surface, intersecting a z-axis at a z-axis intersection point $z_{gp}$.

As used herein, the term "visual representation" means data displayed visually.

As used herein, the term "volumetric cube" means a cube which contains the boundaries of a visual representation of an excavation site.

DETAILED DESCRIPTION OF THE INVENTION

Figure 1:
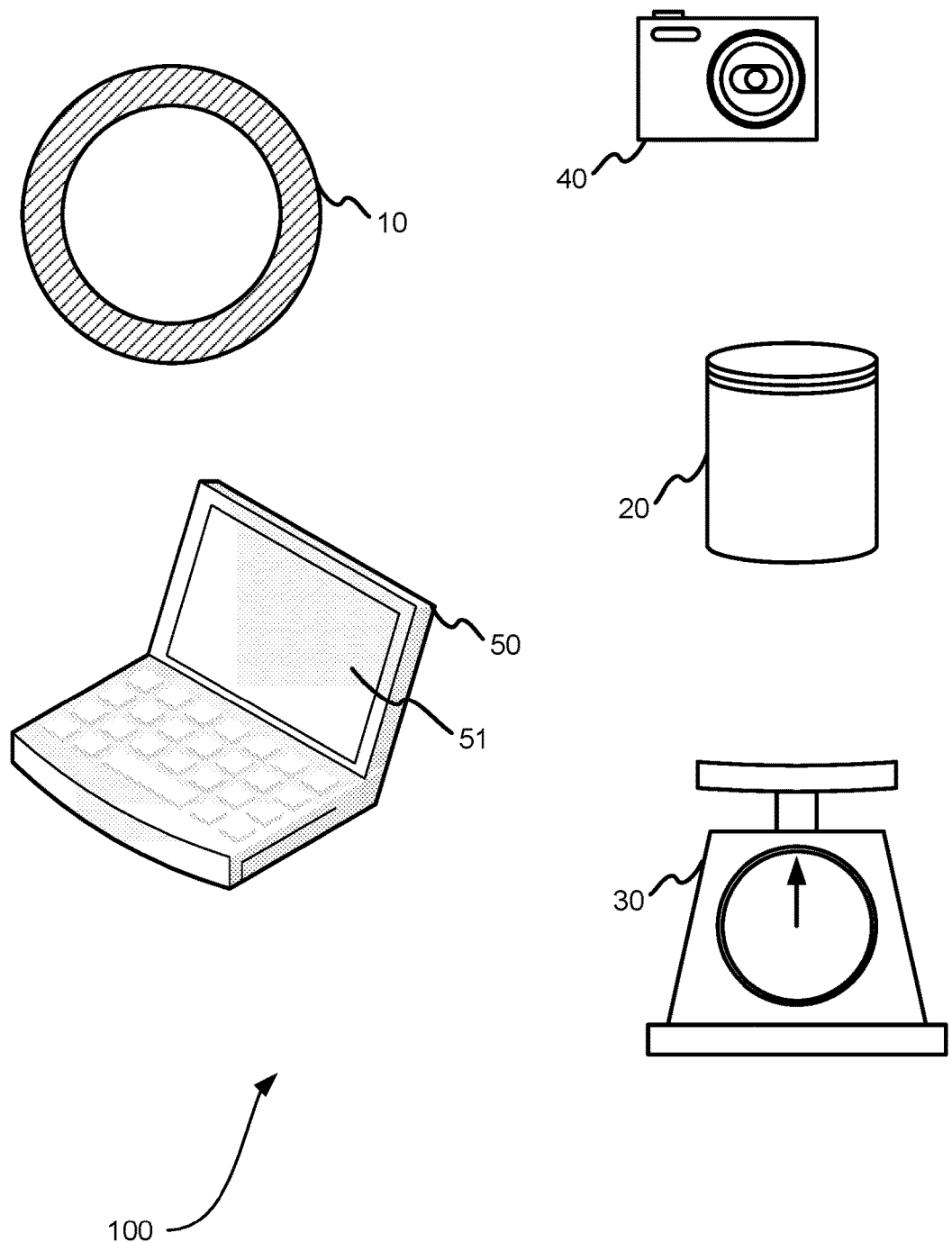
FIG. 1 illustrates an exemplary embodiment of a photogrammetry system.

FIG. 1 illustrates an exemplary embodiment of a photogrammetry system 100. System 100 includes a calibration object 10, a container 20, a mass scale 30, an imaging apparatus 40 and a data processor 50.

Calibration object 10 is any object having a known size. In the exemplary embodiment, calibration object is a flat, annular ring having known inner and outer diameters. The respective dimensions of calibration object 10 vary based on the application, but are large enough to accommodate removal of soil to create an excavation site. In the exemplary embodiment, calibration object 10 is brightly colored to increase contrast and visibility against soil. In certain embodiments, calibration object 10 has a low-reflective coating.

Container 20 is a container having known mass, of sufficient volume to hold all soil removed to create the excavation site. In various embodiments, container 20 is a bowl, box or bag. Placing the soil in container 20 allows measurement of soil mass using scale 30.

Imaging apparatus 40 is a digital imaging apparatus capable of capturing multiple images of the excavation site which form a variant image set. In various embodiments, imaging apparatus 40 is a cell phone camera, still camera, video camera or scanner. Imaging apparatus 40 is connected to data processor 50 or a removable data storage unit, allowing transfer of the images. The connection may be wired or wireless. Optionally, imaging apparatus 40 may include a light source to illuminate the excavation site in low-light conditions.

Data processor 50 is configured with software allowing it to process the images received and determine soil density using a photogrammetry method 200. In the exemplary embodiment, data processor 50 is a laptop computer with a user interface 51.

Figure 2A:
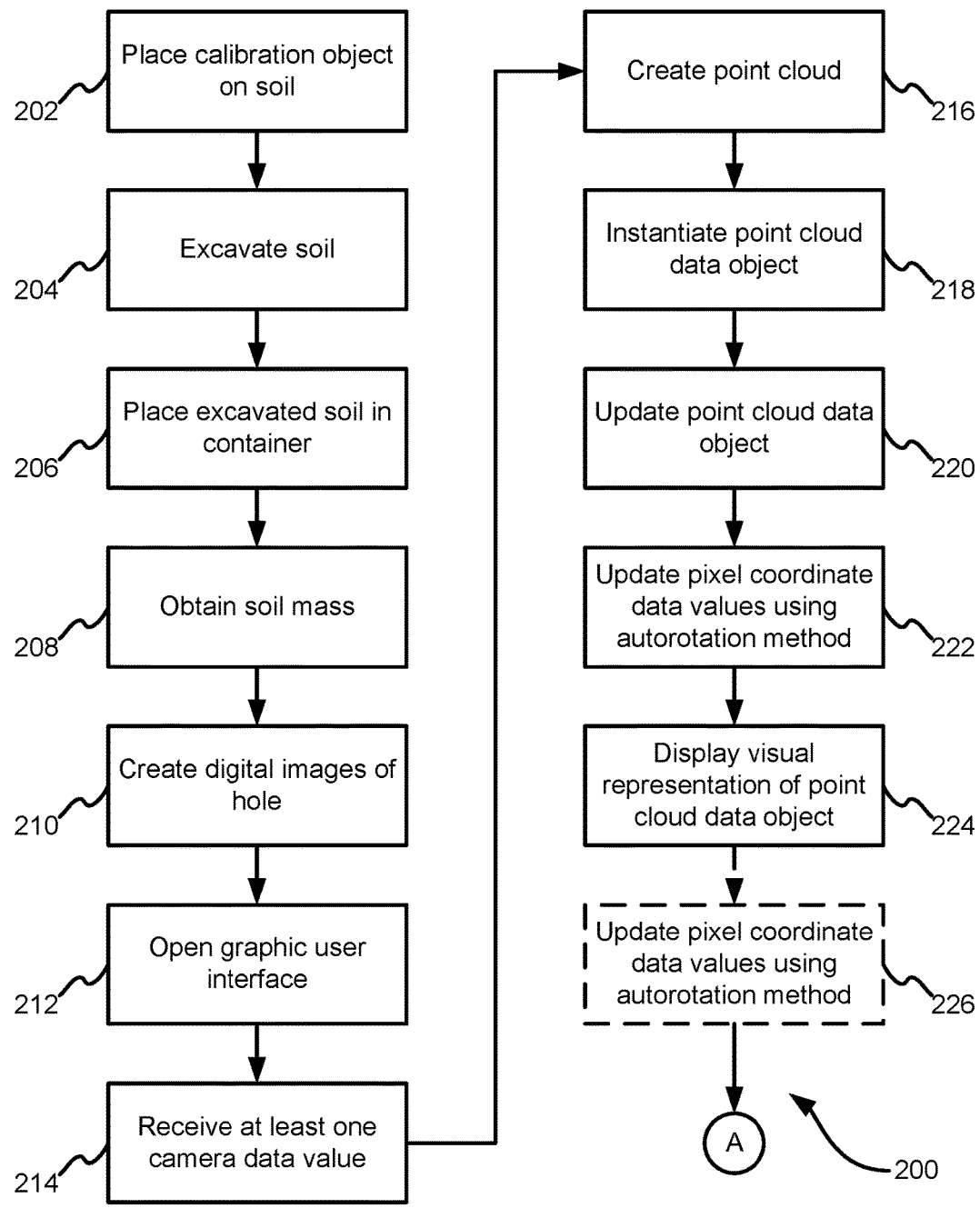
FIGS. 2a and 2b illustrate a flowchart of an exemplary embodiment of a photogrammetry method.
Figure 2B:
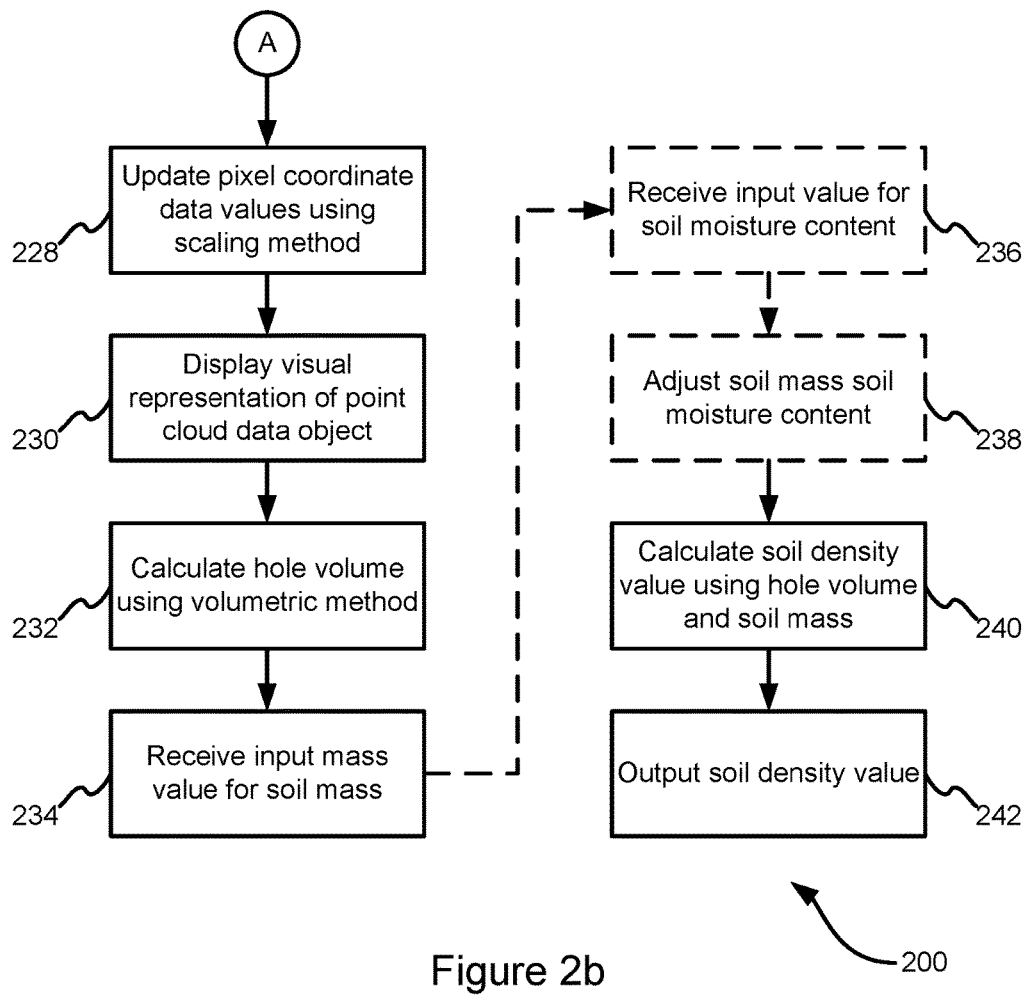

FIGS. 2a and 2b illustrate a flowchart of an exemplary embodiment of photogrammetry method 200.

In step 202, method 200 places calibration object 10 on the upper surface of a soil.

In step 204, method 200 excavates soil to form an excavation site. In the exemplary embodiment, the excavation site is a hole having a convex, substantially conical shape.

In step 206, method 200 places all excavated soil within container 20. In the exemplary embodiment, steps 204 and 206 occur simultaneously.

In step 208, method 200 obtains a soil mass value M of the excavated soil using scale 30.

In step 210, method 200 creates a variant image set from digital images of the excavation site from multiple angles, magnifications and/or elevations. These digital images show both the excavation site and calibration object 10. In the exemplary embodiment, step 210 creates at least 16 images: eight images at a first magnification every 45 degrees and eight images at a second, increased magnification every 45 degrees.

In step 212, method 200 opens a graphic user interface (GUI).

In step 214, method 200 receives at least one camera data value. Camera data values are any metadata describing the camera configuration when the digital images were created. Camera data values may include, but are not limited to, camera make and model, lens aperture, focal length, camera shutter speed, exposure program, focal ratio, lens type, metering mode, flash configuration and ISO sensitivity. These may be entered by a user or automatically retrieved from the digital images.

In step 216, method 200 creates a point cloud from information extracted from each digital image, as well as the camera data values. The point cloud is a plurality of pixels extracted from each digital image. Each pixel has a quasi-unique set of coordinate values along the X-, Y- and Z-axis. Each pixel also has a quasi-unique set of color levels using red, green and blue levels, denoted as R, G and B, respectively.

In step 218, method 200 instantiates a point cloud data object.

In step 220, method 200 updates the point cloud data object with point cloud information extracted from the point cloud. This information includes data values for the pixel identifier, pixel x-coordinate, pixel y-coordinate, pixel z-coordinate, pixel R-level, pixel G-level and pixel B-level.

In step 222, method 200 updates the pixel x-coordinate data values, pixel y-coordinate data values and pixel z-coordinate data values of the point cloud data object using autorotation method 300.

In step 224, method 200 displays a visual representation of the excavation site and said calibration object on the GUI using the point cloud data object. Due to the use of autorotation method 300 in step 220, the visual representation of the surface of the point cloud will appear to be perpendicular to the screen.

In optional step 226, method 200 updates the pixel x-coordinate data values, pixel y-coordinate data values and pixel z-coordinate data values of the point cloud data object using input values for $\theta_x$ and/or $\theta_y$ for steps 306 and/or 312 of autorotation method 300. The input values for $\theta_x$ and/or $\theta_y$ may be predetermined or entered manually.

In step 228, method 200 updates the pixel x-coordinate data values, pixel y-coordinate data values and pixel z-coordinate data values of the point cloud data object using scaling method 400.

In step 230, method 200 displays an updated visual representation on the GUI.

In step 232, method 200 receives plane coordinate values for a user-selected ground plane and calculates an excavated volume $V_h$ using cubic volumetric method 500.

In step 234, method 200 receives an input soil mass value M for the mass of the excavated soil.

In optional step 236, method 200 receives an input value for moisture content $\omega$ of the excavated soil.

In optional step 238, method 200 adjusts the value for mass M of the excavated soil based on the value for moisture content $\omega$ of the excavated soil using the following equation:

$$M = \omega * M_i$$

where $M_i$ is the original mass.

In step 240, method 200 calculates a soil density value D using the excavated volume $V_h$ of the excavation site and soil mass value M.

In step 242, method 200 outputs the soil density value D.

In certain embodiments, method 200 repeats steps 232-242 to obtain a new soil density value D. These steps may be iteratively repeated to provide multiple potential soil density values D. In certain embodiments, method 200 repeats steps 202-242 to obtain a comparative soil density value D for a different excavation site.

Figure 3:
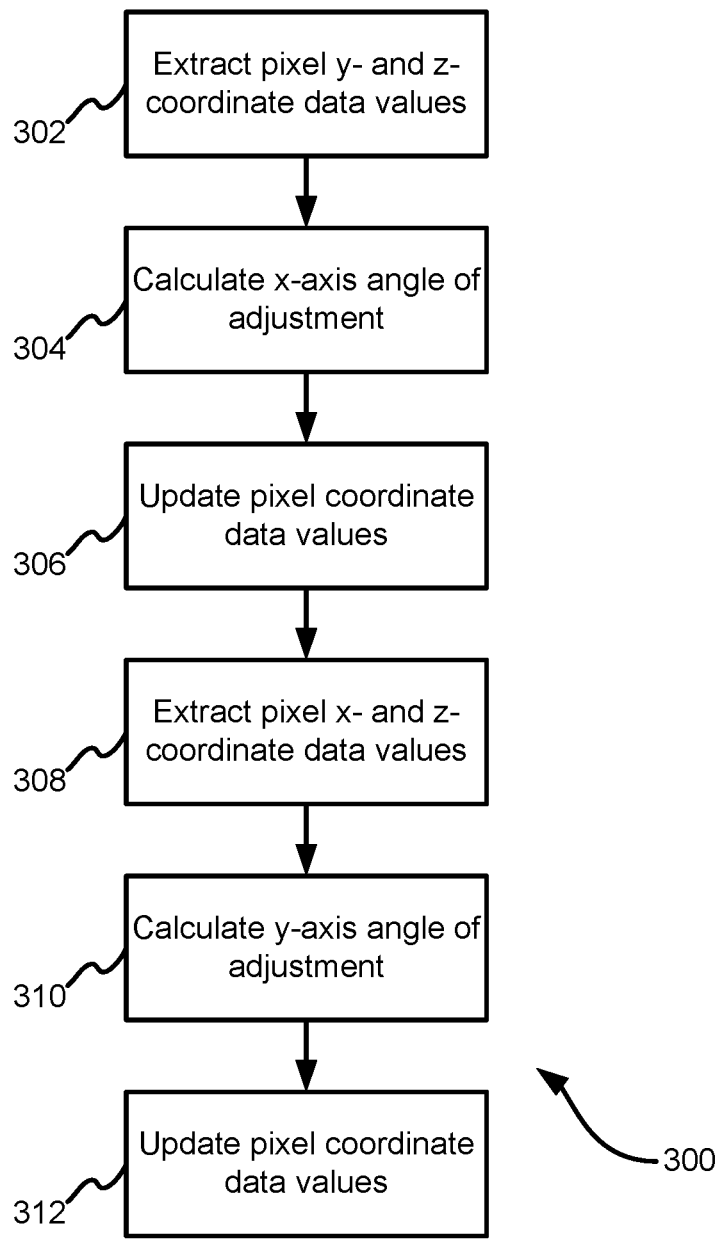
FIG. 3 illustrates a flowchart of an exemplary embodiment of an autorotation method.

FIG. 3 illustrates a flowchart of an exemplary embodiment of autorotation method 300.

In step 302, method 300 extracts the largest pixel y-coordinate data value $y_{max}$ and the smallest pixel y-coordinate data value $y_{min}$ from the point cloud data object, along with the corresponding pixel z-coordinates, $z_{ymax}$ and $z_{ymin}$, respectively.

In step 304, method 300 calculates an x-axis angle of adjustment $\theta_x$ using the following equation:

$$\theta_x = \tan^{-1}\left(\frac{z_{ymax} - z_{ymin}}{y_{max} - y_{min}}\right)$$

In step 306, method 300 updates each pixel x-coordinate, y-coordinate and z-coordinate data value in the point cloud data object with an updated pixel x-coordinate data value $x'_n$, updated pixel y-coordinate data value $y'_n$ and updated pixel z-coordinate data value $z'_n$, respectively, using the equation:

$$\begin{bmatrix} x'_n \\ y'_n \\ z'_n \end{bmatrix} = \begin{bmatrix} x_n \\ y_n \\ z_n \end{bmatrix} * \begin{bmatrix} 1 & 0 & 0 \\ 0 & \cos\theta_x & -\sin\theta_x \\ 0 & \sin\theta_x & \cos\theta_x \end{bmatrix}$$

where $x_n$ is the current pixel x-coordinate data value in the point cloud data object, $y_n$ is the current pixel y-coordinate data value in the point cloud data object, $z_n$ is the current pixel z-coordinate data value in the point cloud data object and n equals the number of pixels.

In step 308, method 300 extracts the largest pixel x-coordinate data value $x_{max}$ and the smallest pixel x-coordinate data value $x_{min}$ from the point cloud data object, along with the corresponding pixel z-coordinates, $z_{xmax}$ and $z_{xmin}$, respectively.

In step 310, method 300 calculates a y-axis angle of adjustment $\theta_y$ using the following equation:

$$\theta_y = \tan^{-1}\left(\frac{z_{xmax} - z_{xmin}}{x_{max} - x_{min}}\right)$$

In step 312, method 300 updates each pixel x-coordinate, y-coordinate and z-coordinate data value in the point cloud data object with an updated pixel x-coordinate data value $x'_n$, updated pixel y-coordinate data value $y'_n$ and updated pixel z-coordinate data value $z'_n$, respectively, using the equation:

$$\begin{bmatrix} x'_n \\ y'_n \\ z'_n \end{bmatrix} = \begin{bmatrix} x_n \\ y_n \\ z_n \end{bmatrix} * \begin{bmatrix} \cos\theta_y & 0 & -\sin\theta_y \\ 0 & 1 & 0 \\ \sin\theta_y & 0 & \cos\theta_y \end{bmatrix}$$

Figure 4:
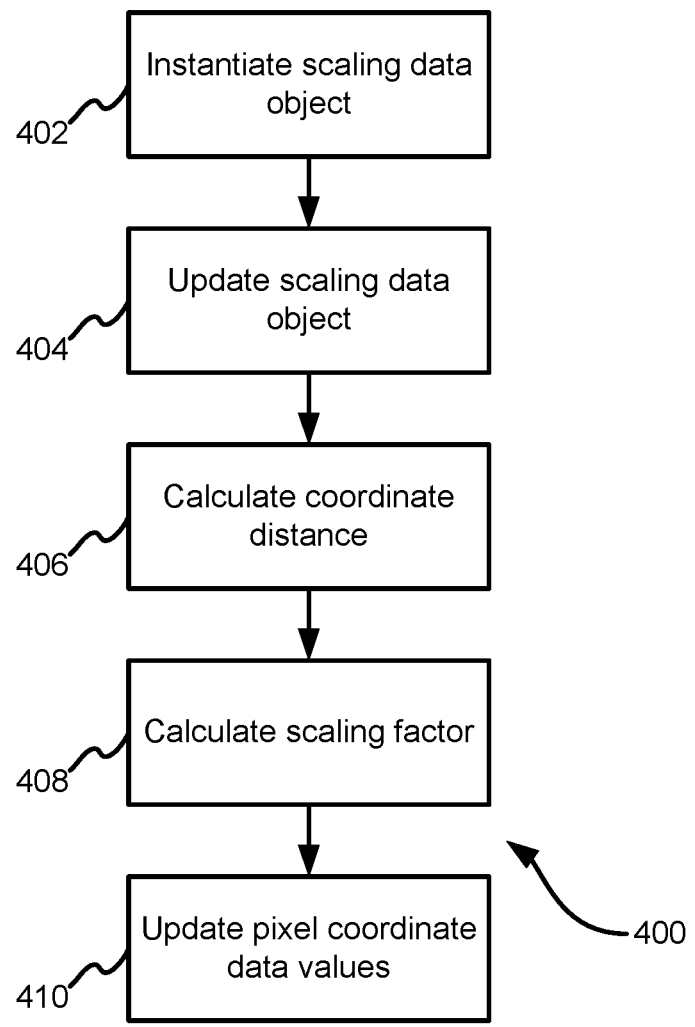
FIG. 4 illustrates a flowchart of an exemplary embodiment of a scaling method.

FIG. 4 illustrates a flowchart of an exemplary embodiment of scaling method 400.

In step 402, method 400 instantiates a scaling data object.

In step 404, method 400 updates the scaling data object with data values for outer point x-coordinate $x_o$, outer point y-coordinate $y_o$, inner point x-coordinate $x_i$, inner point y-coordinate $y_i$ and a scale value S. Scale value S is a known quantity. In the exemplary embodiment, scale value S is the distance between two opposing sides of calibration object 10. In other embodiments, scale value S may be a distance along a linear object, or a distance between two defined points on an object.

In one embodiment, a user manually enters the data values for outer point x-coordinate $x_o$, outer point y-coordinate $y_o$, inner point x-coordinate $x_i$, inner point y-coordinate $y_i$ and a scale value S. In another embodiment, at least one of the data values for outer point x-coordinate $x_o$, outer point y-coordinate $y_o$, inner point x-coordinate $x_i$, inner point y-coordinate $y_i$ and a scale value S is entered manually and at least one of the data values for outer point x-coordinate $x_o$, outer point y-coordinate $y_o$, inner point x-coordinate $x_i$, inner point y-coordinate $y_i$ and a scale value S is entered by clicking on a point on the visual representation of the point cloud data object on the GUI.

In step 406, method 400 calculates a coordinate distance C between an inner point and an outer point using the equation:

$$C = \sqrt{(x_o - x_i)^2 + (y_o - y_i)^2}$$

In step 408, method 400 calculates a scaling factor $F_s$ using the equation:

$$F_s = S/C$$

In step 410, method 400 updates data values for the pixel x-coordinate, pixel y-coordinate, pixel z-coordinate by multiplying each pixel x-coordinate data value, pixel y-coordinate data value and pixel z-coordinate data value in the point cloud data object by scaling factor $F_s$.

Figure 5:
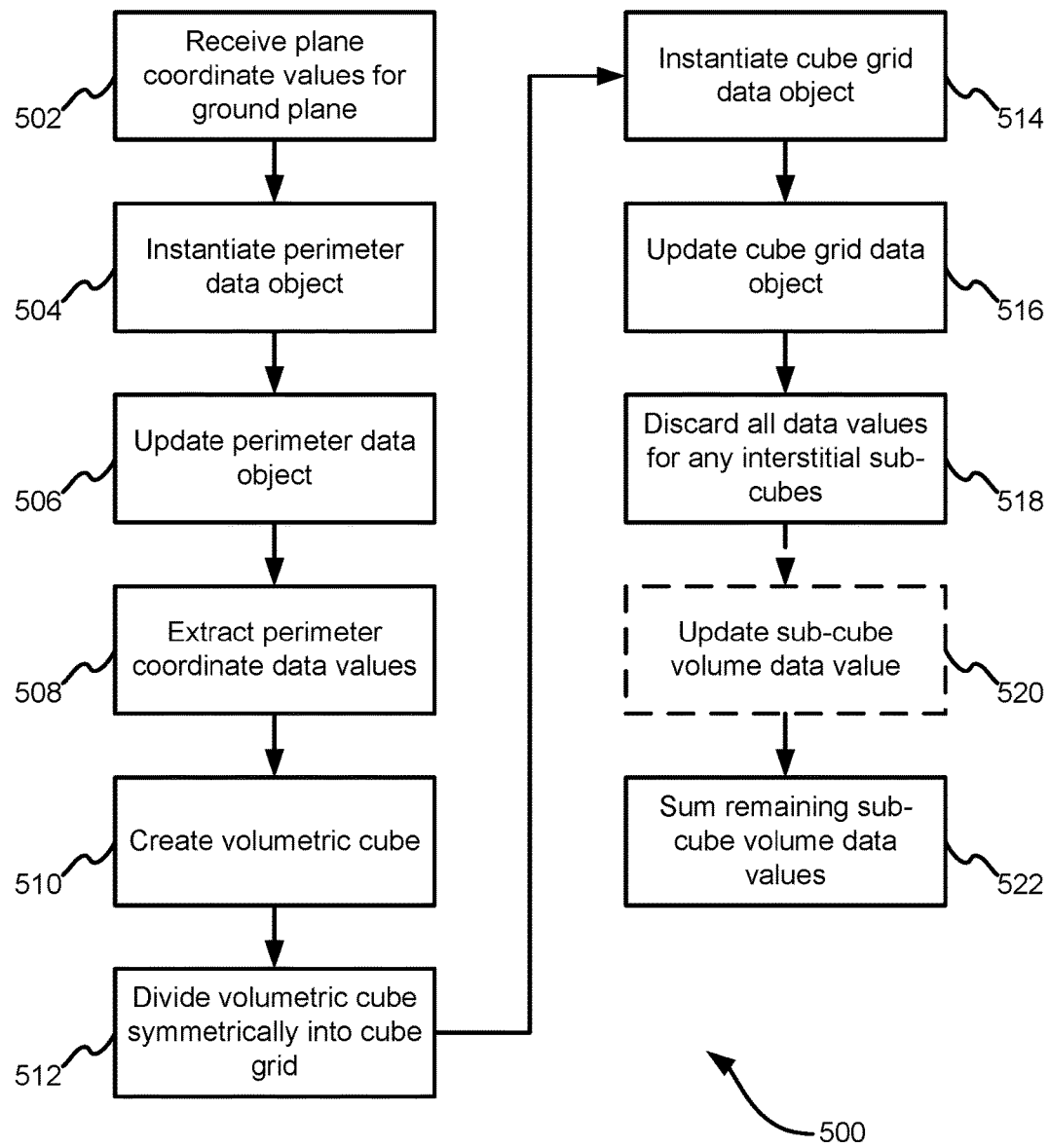
FIG. 5 illustrates a flowchart of an exemplary embodiment of a cubic volumetric method.

FIG. 5 illustrates a flowchart of an exemplary embodiment of cubic volumetric method 500.

In step 502, method 500 receives plane coordinate values for a user-selected ground plane. In the exemplary embodiment, a user utilizes a slider bar on a GUI to move a visual plane representation along the Z-axis through the visual representation of the excavation site and calibration object. The user moves the slider bar until the ground plane intersects the perimeter of the excavation site.

In step 504, method 500 instantiates a perimeter data object.

In step 506, method 500 updates the perimeter data object with information extracted from the point cloud data object. This information includes data values for the pixel identifier, pixel x-coordinate and pixel y-coordinate of pixels that intersect the user-selected ground plane.

In step 508, method 500 extracts the largest perimeter x-coordinate data value $x_{pmax}$, the smallest perimeter x-coordinate data value $x_{pmin}$, the largest perimeter y-coordinate data value $y_{pmax}$, the smallest perimeter y-coordinate data value $y_{pmin}$ from the perimeter data object.

In step 510, method 500 creates a volumetric cube having outer boundaries defined by the largest perimeter x-coordinate data value $x_{pmax}$, the smallest perimeter x-coordinate data value $x_{pmin}$, the largest perimeter y-coordinate data value $y_{pmax}$, the smallest perimeter y-coordinate data value $y_{pmin}$, z-axis intersection point $z_{gp}$, and the smallest z-coordinate data value $z_{min}$ from the point cloud data object.

In step 512, method 500 divides the volumetric cube symmetrically into a cube grid comprising a plurality of sub-cubes having identical volume. The number of sub-cubes may be entered manually, selected from a menu or preprogrammed. Each sub-cube is located between the largest perimeter x-coordinate data value $x_{pmax}$, the smallest perimeter x-coordinate data value $x_{pmin}$, the largest perimeter y-coordinate data value $y_{pmax}$, the smallest perimeter y-coordinate data value $y_{pmin}$, z-axis intersection point $z_{gp}$, and the smallest z-coordinate data value $z_{min}$. The boundaries of each sub-cube are defined by a largest perimeter x-coordinate data value $x_{cmax}$, a smallest perimeter x-coordinate data value $x_{cmin}$, a largest perimeter y-coordinate data value $y_{cmax}$, a smallest perimeter y-coordinate data value $y_{cmin}$, a largest perimeter z-coordinate data value $z_{cmax}$ and a smallest perimeter z-coordinate data value $z_{cmin}$.

In step 514, method 500 instantiates a cube grid data object.

In step 516, method 500 updates the cube grid data object with cube grid information extracted from the cube grid. This information includes data values for the sub-cube identifier, the sub-cube volume, the largest sub-cube perimeter x-coordinate data value $x_{cmax}$, the smallest sub-cube perimeter x-coordinate data value $x_{cmin}$, the largest sub-cube perimeter y-coordinate data value $y_{cmax}$, the smallest sub-cube perimeter y-coordinate data value $y_{cmin}$, the largest sub-cube perimeter z-coordinate data value $z_{cmax}$ and the smallest sub-cube perimeter z-coordinate data value $z_{cmin}$.

In step 518, method 500 discards all data values for any sub-cubes located directly between the point cloud and the volumetric cube, as determined by the largest sub-cube perimeter x-coordinate data value $x_{cmax}$, the smallest sub-cube perimeter x-coordinate data value $x_{cmin}$, the largest sub-cube perimeter y-coordinate data value $y_{cmax}$, the smallest sub-cube perimeter y-coordinate data value $y_{cmin}$, the largest sub-cube perimeter z-coordinate data value $z_{cmax}$ and the smallest sub-cube perimeter z-coordinate data value $z_{cmin}$. Method 500 removes all data values for discarded sub-cubes from the cube grid data object.

In optional step 520, method 500 updates the sub-cube volume data value of any sub-cubes that pass through pixels in the point cloud to exclude any volume located directly between the point cloud and the volumetric cube.

In step 522, method 500 sums the remaining sub-cube volume data values to calculate the excavated volume $V_h$.

It will be understood that many additional changes in the details, materials, procedures and arrangement of parts, which have been herein described and illustrated to explain the nature of the invention, may be made by those skilled in the art within the principle and scope of the invention as expressed in the appended claims.

It should be further understood that the drawings are not necessarily to scale; instead, emphasis has been placed upon illustrating the principles of the invention. Moreover, the term "substantially" as used herein may be applied to modify any quantitative representation that could permissibly vary without resulting in a change in the basic function to which it is related.

What is claimed is:

1. A computer apparatus for analyzing soil density utilizing a user-selected ground plane, comprised of:
   a photogrammetric data processor configured with software to perform a photogrammetry method, said photogrammetry method comprising the steps of:
   receiving a variant image set of a calibration object and excavation site;
   creating a point cloud from said variant image set and at least one camera data value;
   instantiating a point cloud data object with point cloud data values to display a visual representation of said excavation site and said calibration object on a graphic user interface (GUI);
   a first processor which receives plane coordinate values representing plane parameters and performs functions to transform said plane coordinate values to produce a volumetric cube data set which contains cube perimeter coordinate data values representing a volumetric cube, wherein one or more of said perimeter coordinate data values correspond to said plane coordinate values;
   a cube grid data object having processing capability, configured to receive said volumetric cube data set and perform functions to transform said cube perimeter coordinate data values into a sub-cube data set to populate a cube grid data structure with sub-cube perimeter coordinate data values and volume values associated with each of said sub-cubes; and
   a density processing component configured to receive a soil mass value M of excavated soil and said cube grid data structure and to perform functions to discard sub-cube values that are not within designated point cloud parameters and to calculate excavated volume $V_h$ and soil density value D based on remaining sub-cube values and said soil mass value M.

2. The apparatus of claim 1, wherein said first processor is further configured with a photogrammetry processing component which is configured to receive updated plane coordinate values and re-calculate said soil density value D.

3. The apparatus of claim 1 wherein said first processor is further configured to iteratively receive updated plane coordinate values and iteratively re-calculate said soil density value D.

4. The apparatus of claim 1, which further includes a processor for updating a plurality of pixel x-coordinate data values, a plurality of pixel y-coordinate data values and a plurality of pixel z-coordinate data values of said cloud data object using an autorotation method.

5. The apparatus of claim 4, which further includes a processor configured to:
   extract a largest pixel y-coordinate data value $Y_{max}$ and a smallest pixel y-coordinate data value $Y_{min}$ from said point cloud data object, along with a plurality of corresponding pixel z-coordinates, $Z_{ymax}$ and $Z_{ymin}$, respectively,
   update each of said plurality of pixel x-coordinate data values, said plurality of y-coordinate data values and said plurality of z-coordinate data values in said point cloud data object with an updated pixel x-coordinate data value $x'_n$, updated pixel y-coordinate data value $y'_n$ and updated pixel z-coordinate data value $z'_n$, respectively, using the equation:

$$\begin{bmatrix} x'_n \\ y'_n \\ z'_n \end{bmatrix} = \begin{bmatrix} x_n \\ y_n \\ z_n \end{bmatrix} * \begin{bmatrix} 1 & 0 & 0 \\ 0 & \cos\theta_x & -\sin\theta_x \\ 0 & \sin\theta_x & \cos\theta_x \end{bmatrix}$$

wherein $x_n$ is said current pixel x-coordinate data value in said point cloud data object, $y_n$ is said current pixel y-coordinate data value in said point cloud data object, $z_n$ is said current pixel z-coordinate data value in said point cloud data object, n equals said number of pixels and $\theta_x$ is an x-axis angle of adjustment;

extract a largest pixel x-coordinate data value $x_{max}$ and a smallest pixel x-coordinate data value $x_{min}$ from said point cloud data object, along with a plurality of corresponding pixel z-coordinates, $z_{xmax}$ and $z_{xmin}$, respectively;

update each of said plurality of pixel x-coordinate data values, said plurality of y-coordinate data values and said plurality of z-coordinate data values in said point cloud data object with an updated pixel x-coordinate data value $x'_n$, an updated pixel y-coordinate data value $y'_n$ and an updated pixel z-coordinate data value $z'_n$, respectively, using the equation:

$$\begin{bmatrix} x'_n \\ y'_n \\ z'_n \end{bmatrix} = \begin{bmatrix} x_n \\ y_n \\ z_n \end{bmatrix} * \begin{bmatrix} \cos\theta_y & 0 & -\sin\theta_y \\ 0 & 1 & 0 \\ \sin\theta_y & 0 & \cos\theta_y \end{bmatrix}$$

wherein $\theta_y$ is a y-axis angle of adjustment.

6. The apparatus of claim 5, which further includes a processor configured to calculate at least one of said x-axis angle of adjustment $\theta_x$ and said y-axis angle of adjustment $\theta_y$ using at least one of the equations:

$$\theta_x = \tan^{-1}\left(\frac{z_{ymax} - z_{ymin}}{y_{max} - y_{min}}\right)$$

$$\theta_y = \tan^{-1}\left(\frac{z_{xmax} - z_{xmin}}{x_{max} - x_{min}}\right).$$

7. The apparatus of claim 1, which further includes a processor for receiving an input moisture value for a moisture content w of said excavated soil.

8. The apparatus of claim 7, which further includes a processor for adjusting said value for mass M of said excavated soil based on said value for moisture content w of said excavated soil.

9. The apparatus of claim 1, which further includes a processor configured to perform a scaling method comprised of the steps of:

instantiating a scaling data object;

updating said scaling data object with data values for outer point x-coordinate $x_o$, outer point y-coordinate $y_c$, inner point x-coordinate $x_i$, inner point y-coordinate y, and a scale value S, wherein said scale value S is a known quantity;

calculating a coordinate distance C between an inner point and an outer point using the equation:

$$C = \sqrt{(x_o - x_i)^2 + (y_o - y_i)^2}$$

calculating a scaling factor $F_S$ using the equation:

$$F_S = S/C$$

updating each of said plurality of pixel x-coordinate data values, each of said plurality of pixel y-coordinate data values and each of said plurality of pixel z-coordinate data values by multiplying each of said plurality of pixel x-coordinate data values, each of said plurality of pixel y-coordinate data values and each of said plurality of pixel z-coordinate data values in said point cloud data object by said scaling factor $F_S$.

10. The apparatus of claim 9, wherein at least one of said data values for outer point x-coordinate $X_o$, outer point y-coordinate $y_o$, inner point x-coordinate $X_i$, inner point y-coordinate $Y$, and a scale value S is entered manually and at least one of said data values for outer point x-coordinate $X_o$, outer point y-coordinate $y_o$, inner point x-coordinate $X_i$, inner point y-coordinate Y, and a scale value S is entered by clicking on a point on said visual representation of said point cloud data object on said GUI.

11. The apparatus of claim 1, further comprising a calibration object, wherein said calibration object has a low-reflective coating.

12. The apparatus of claim 1, further comprising a calibration object, wherein said calibration object is a flat, annular ring having known inner and outer diameters.

* * * * *